United States Patent
Lennox et al.

[11] Patent Number: 5,955,379
[45] Date of Patent: Sep. 21, 1999

[54] BIOSENSOR DEVICE AND METHOD

[75] Inventors: R. Bruce Lennox, Montreal; Robert S. Hodges, Edmonton; Randall T. Irvin, Sherwood Park; Glen Armstrong, Edmonton; David R. Bundle, Edmonton; Pavel Kitov, Edmonton; Craig Railton, Edmonton, all of Canada

[73] Assignees: McGill University, Montreal; Pence, Edmonton, both of Canada

[21] Appl. No.: 08/845,659

[22] Filed: Apr. 24, 1997

Related U.S. Application Data

[60] Provisional application No. 60/016,384, Apr. 25, 1996.

[51] Int. Cl.[6] .................................................. G01N 33/533
[52] U.S. Cl. ........................ 436/528; 436/518; 436/525; 436/528; 436/807; 436/806; 436/904; 435/7.1; 435/7.5; 427/2.11; 422/82.02
[58] Field of Search ..................................... 436/518, 525, 436/528, 807, 806, 904; 435/7.1, 7.5; 427/2.11; 422/82.02

[56] References Cited

U.S. PATENT DOCUMENTS

| | | |
|---|---|---|
| 4,789,804 | 12/1988 | Karube et al. . |
| 5,089,112 | 2/1992 | Skotkeim et al. . |
| 5,204,239 | 4/1993 | Gitler et al. .............................. 435/7.1 |
| 5,242,828 | 9/1993 | Bergstrom et al. ....................... 435/291 |
| 5,268,305 | 12/1993 | Ribi et al. . |
| 5,313,264 | 5/1994 | Ivarsson et al. . |
| 5,368,712 | 11/1994 | Tomich et al. .......................... 204/403 |
| 5,401,378 | 3/1995 | King et al. . |
| 5,436,161 | 7/1995 | Bergstrom et al. . |
| 5,436,170 | 7/1995 | Cornell et al. .......................... 436/527 |
| 5,478,756 | 12/1995 | Gizeli et al. . |
| 5,485,277 | 1/1996 | Foster . |
| 5,491,097 | 2/1996 | Ribi et al. .............................. 436/518 |
| 5,492,840 | 2/1996 | Malmqvist et al. . |
| 5,514,501 | 5/1996 | Tarlov .......................................... 430/5 |
| 5,567,301 | 10/1996 | Stetter et al. . |
| 5,571,568 | 11/1996 | Ribi et al. . |

FOREIGN PATENT DOCUMENTS

| | | |
|---|---|---|
| WO 89/01159 | 2/1989 | WIPO . |
| WO 90/05303 | 5/1990 | WIPO . |
| WO 96/02830 | 2/1996 | WIPO . |
| WO 96/09547 | 3/1996 | WIPO . |
| WO 96/10178 | 4/1996 | WIPO . |
| WO 97/01092 | 1/1997 | WIPO . |
| WO 97/02359 | 1/1997 | WIPO . |
| WO 94/07593 | 4/1997 | WIPO . |

OTHER PUBLICATIONS

CRC Handbook of Chemistry and Physics, 67th edition, CRC Press, Inc., Boca Raton, Florida, pp. D151, D153, D155–D158, 123, 127, 1986.

Dakkouri, A.S et al., "Scanning Tunneling Microscopy Study of L-Cysteine on Au(111)," Langmuri, 12,:2849–2852, 1996.

Khilko, S, et al., "Measuring interaction of MHC class I molecules using surface plasmon resonance", J. Immunological Methods, 183 (1995).

*Primary Examiner*—James C. Housel
*Assistant Examiner*—Bao-Thuy L. Nguyen
*Attorney, Agent, or Firm*—Peter J. Dehlinger; John F. Brady

[57] ABSTRACT

A biosensor apparatus for detecting a binding event between a ligand and receptor. The apparatus includes an electrode substrate coated with a high-dielectric hydrocarbon-chain monolayer, and having ligands attached to the exposed monolayer surface. Binding of a receptor to the monolayer-bound ligand, and the resultant perturbation of the monolayer structure, causes ion-mediated electron flow across the monolayer. In one embodiment, the monolayers have a coil—coil heterodimer embedded therein, one subunit of which is attached to the substrate, and the second of which carries the ligand at the monolayer surface.

10 Claims, 11 Drawing Sheets

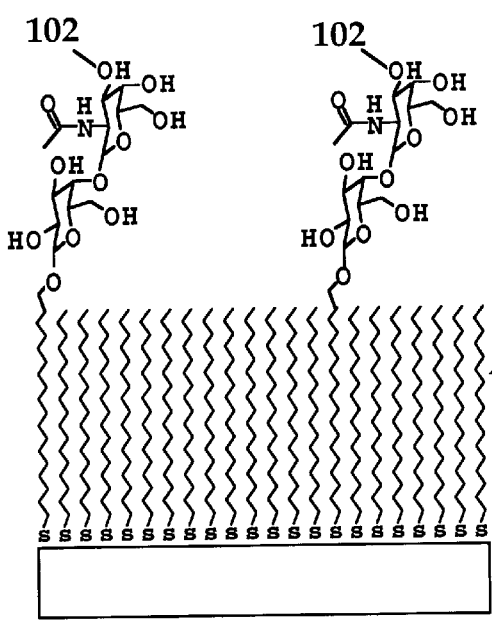
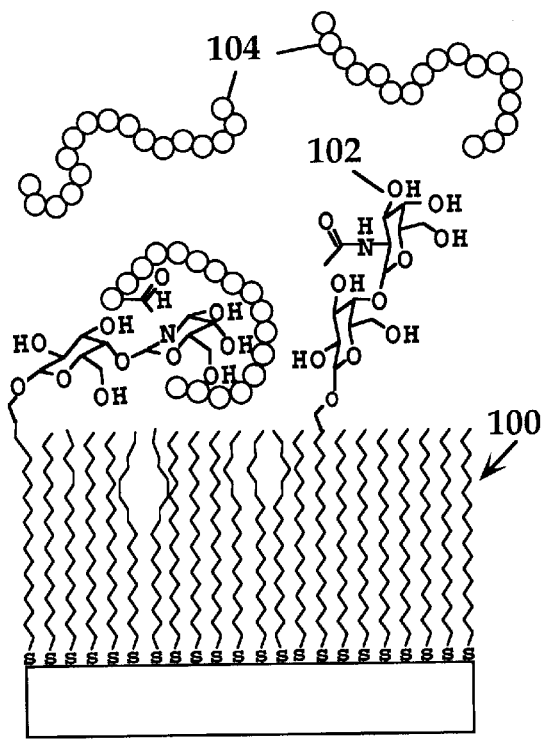
Fig. 6A  Fig. 6B
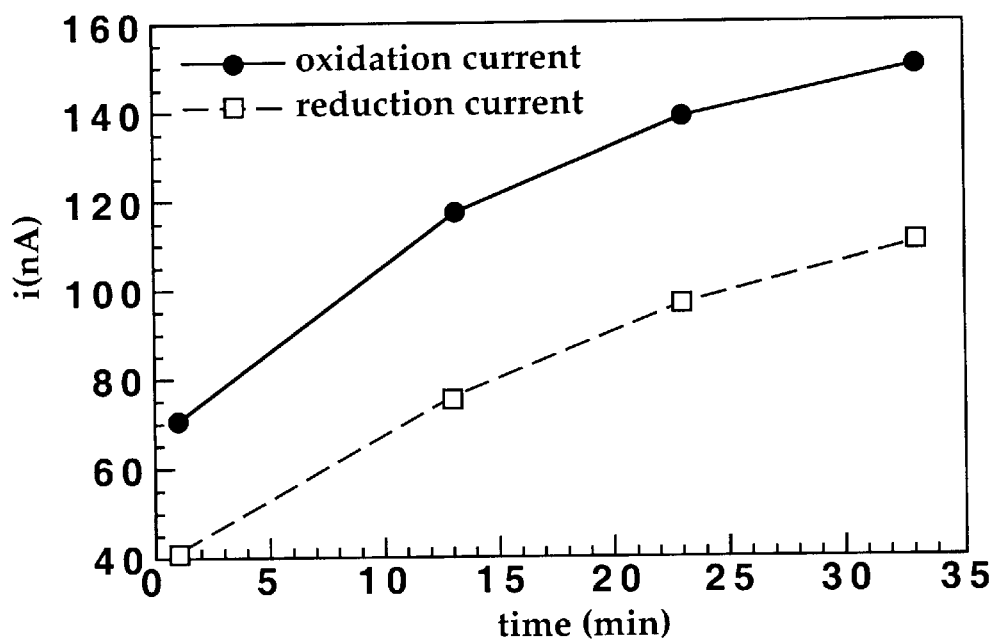
Fig. 7

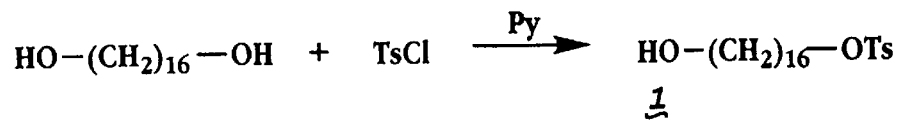
Fig. 17A
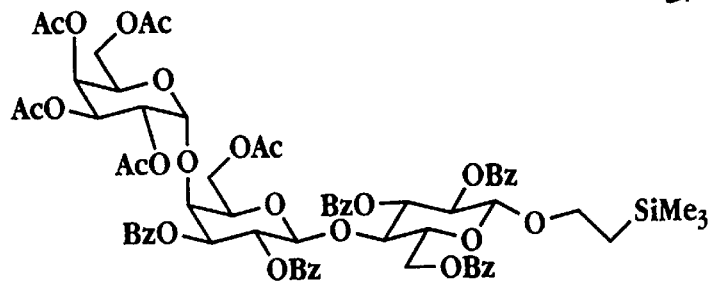
Fig. 17B
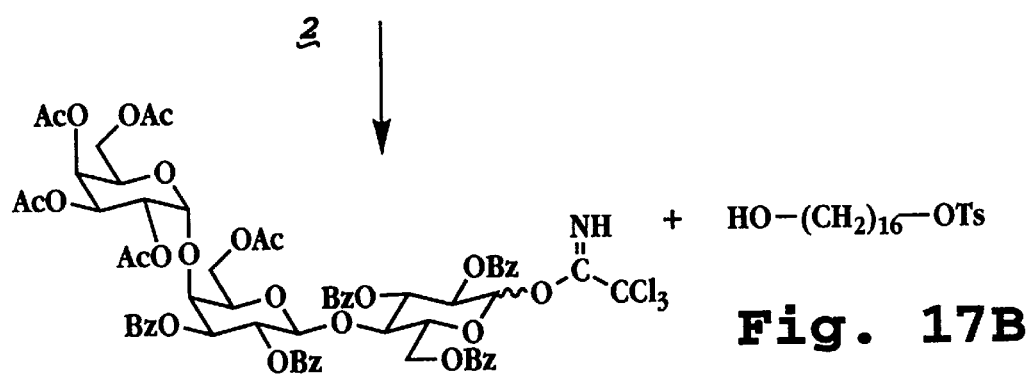
Fig. 17C
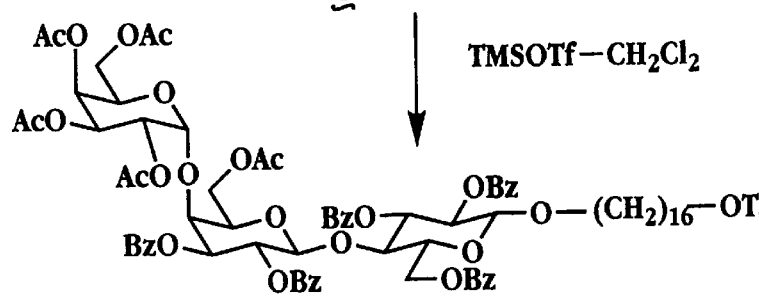
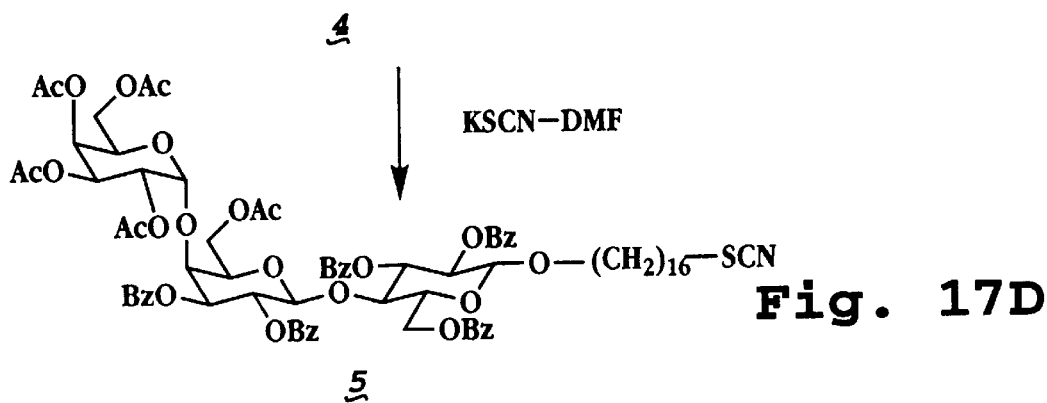
Fig. 17D

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 35 amino acids
       (B) TYPE: amino acid
       (C) STRANDEDNESS: single
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: EE peptide (xi) SEQUENCE DESCRIPTION: SEQ ID NO:1:

Glu Val Glu Ala Leu Gln Lys Glu Val Ser Ala Leu Glu Lys Glu Val
1               5                   10                  15

Ser Ala Leu Glu Cys Glu Val Ser Ala Leu Glu Lys Glu Val Glu Ala
            20                  25                  30

Leu Gln Lys
        35

(2) INFORMATION FOR SEQ ID NO:2:

(i) SEQUENCE CHARACTERISTICS:
       (A) LENGTH: 35 amino acids
       (B) TYPE: amino acid
       (C) STRANDEDNESS: single
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: KK peptide (xi) SEQUENCE DESCRIPTION: SEQ ID NO:2:

Lys Val Glu Ala Leu Lys Lys Val Ser Ala Leu Lys Glu Lys Val
1               5                   10                  15

Ser Ala Leu Lys Cys Lys Val Ser Ala Leu Lys Glu Lys Val Glu Ala
            20                  25                  30

Leu Lys Lys
        35

BIOSENSOR DEVICE AND METHOD

This application claims the priority of U.S. Provisional Application No. 60/016,384 filed Apr. 25, 1996, which is incorporated herein by reference.

FIELD OF THE INVENTION

The present invention relates to biosensors, in particular, to a biosensor for measuring a binding event between a ligand and a ligand-binding receptor, and to methods employing such biosensor.

BACKGROUND OF THE INVENTION

To a great extent, diagnostic tools used for detecting or quantitating biological analytes are based on ligand-specific binding between a ligand and a receptor. Ligand-receptor binding pairs used commonly in diagnostics include antigen-antibody, hormone-receptor, drug-receptor, cell surface antigen-lectin, biotin-avidin, and complementary nucleic acid strands, wherein said ligand is typically the smaller of the two binding pair members. The analyte to be detected may be either member of the binding pair; alternatively, the analyte may be a ligand analog that competes with the ligand for binding to the complement receptor.

A variety of methods for detecting ligand/receptor interactions have been developed. The simplest of these is a solid-phase format employing a reporter-labeled ligand whose binding to or release from a solid surface is triggered by the presence of analyte ligand or receptor. In a typical solid-phase sandwich type assay, for example, the analyte to be measured is a ligand with two or more binding sites, allowing ligand binding both to a receptor, e.g., antibody, carried on a solid surface, and to a reporter-labeled second receptor. The presence of analyte is detected (or quantitated) by the presence (or amount) of reporter bound to solid surface.

In a typical solid-phase competitive binding assay, an analyte ligand (or receptor) competes with a reporter-labeled analyte analog for binding to a receptor (or ligand) carried on a solid support. The amount of reporter signal associated with the solid support is inversely proportional to the amount of sample analyte to be detected or determined.

The reporter label used in both solid-phase formats is typically a visibly detectable particle or an enzyme capable of converting a substrate to an easily detectable product. Simple spectrophotometric devices allow for the quantitation of the amount of reporter label, for quantifying amount of analyte.

Detecting or quantitating ligand-specific binding events is also important in high-throughput methods being developed for combinatorial library screening. In a typical method, a large library of possible effector molecules (ligands) is synthesized. The library members are then screened for effector activity by their ability to bind to a selected receptor. The approach has the potential to identify, for example, new oligopeptide antigens capable of high-specificity binding to disease related antibodies, or small-molecule compounds capable of interacting with a selected pharmacological target, such as a membrane bound receptor or cellular enzyme.

High-throughput screening methods typically employ simple ligand displacement assays to detect and quantitate ligand binding to a receptor. Displacement assays have the advantage of high sensitivity, e.g., where the displaced ligand is radiolabeled, and also allow for the determination of ligand-receptor binding affinity, based on competitive displacement of a binding agent whose binding affinity to the target receptor is known.

In both diagnostics and high-throughput screening, there is increasing interest in developing electrochemical biosensors capable of detecting and quantifying ligand-receptor binding events. Such biosensors are designed to produce electrical signals in response to a selected analyte-specific event, such as a ligand-receptor binding event. The interest in biosensors is spurred by a number of potential advantages over strictly biochemical assay formats, such as those discussed above.

First, biosensors may be produced, using conventional microchip technology, in highly reproducible and miniaturized form, with the capability of placing a large number of biosensor elements on a single substrate.

Secondly, because small electrochemical signals can be readily amplified (and subjected to various types of signal processing if desired), biosensors have the potential for measuring minute quantities of analyte, and proportionately small changes in analyte levels.

A consequence of the features above is that a large number of different analytes can be detected or quantitated by applying a small sample volume, e.g., 10–50 $\mu$l, to a single multi-sensor chip.

Heretofore, electrochemical biosensors have been more successfully applied to detecting analytes that are themselves electrochemical species, or can be participate in catalytic reactions that generate electrochemical species, than to detecting ligand-receptor binding events. This is not surprising, given the more difficult challenge of converting a biochemical binding event to an electrochemical signal. One approach to this problem is to provide two separate reaction elements in the biosensor: a first element contains a receptor and bound enzyme-linked ligand, and the second element, components for enzymatically generating and then measuring an electrochemical species. In operation, analyte ligand displaces the ligand-enzyme conjugate from the first element, releasing the enzyme into the second element region, thus generating an electrochemical species which is measured in the second element.

Two-element biosensors of this type are relatively complicated to produce, particularly by conventional silicon-wafer methods, since one or more biological layers and permselective layers must be deposited as part of the manufacturing process. Further, enzymes or receptors in the biosensor can denature on storage, and the device may have variable "wetting" periods after a sample is applied.

Biosensors that attempt to couple electrochemical activity directly to a ligand-receptor binding event, by means of gated membrane electrodes, have been proposed. For example, U.S. Pat. Nos. 5,204,239 and 5,368,712 disclose gated membrane electrodes formed of a lipid bilayer membrane containing an ion-channel receptor that is either opened or closed by ligand binding to the receptor. Electrodes of this type are difficult to make and store, and are limited at present to a rather small group of receptor proteins.

Alternatively, direct ligand/receptor binding may be measured electrically by embedding the receptor in a thin polymer film, and measuring changes in the film's electrical properties, e.g., impedance, due to ligand binding to the receptors. U.S. Pat. No. 5,192,507 is exemplary. Since ligand binding to the receptor will have a rather small effect on film properties, and since no amplification effect is achieved, the approach is expected to have limited sensitivity.

It would thus be desirable to provide a biosensor capable of detecting and quantifying ligand-binding events and characterized by: (i) direct electrochemical conversion of the binding event to electrical signal; (ii) a high electron flow "turnover" from each binding event; (iii) adaptable to substantially any ligand, and (iv) good storage characteristics and rapid wetting with sample application. In addition, the device should be easily produced, and preferably amenable to manufacture using standard microchip technologies.

SUMMARY OF THE INVENTION

One aspect of the invention is a biosensor apparatus for detecting a binding event between a ligand and ligand-binding receptor. An electrode in the apparatus includes an electrode substrate with a detection surface covered by a monolayer of hydrocarbon chains. The chains are anchored at their proximal ends to the detection surface, and are sufficiently close-packed and ordered to form an effective barrier to electron flow across the monolayer mediated by a redox ion species in an aqueous solution in contact with the monolayer.

The ligand whose binding to a receptor is to be detected is attached to the distal ends of a portion of the monolayer chains, such that binding of a ligand-binding receptor to ligand perturbs the monolayer sufficiently to measurably increase electron flow across the monolayer mediated by such redox ion species.

The aqueous solution of redox species in contact with the monolayer is held in a chamber that is also designed to receive sample receptor, to bring the receptor into contact with ligand on the monolayer. Ion-mediated electron flow across said monolayer, in response to binding events occurring between said receptor and ligand, is measured in an electrical circuit in the apparatus.

In a preferred embodiment, the monolayer is composed of 8–22 carbon atom chains attached at their proximal ends to the detection surface, e.g., a gold surface, by a thiolate linkage. The chains have a preferred molecular density of about 3 to 5 chains/nm$^2$.

The dielectric constant of the monolayer in the presence of the solution of redox species, but in the absence of the binding receptor, is preferably less than about 2, with a change in the dielectric constant of 10% or more, by receptor binding to the ligand, being readily detectable.

Exemplary ligand-receptor pairs include antigen-antibody, hormone-receptor, drug-receptor, cell-surface antigen-lectin, biotin-avidin, substrate/antibody and complementary nucleic acid strands, where the ligand is typically the first-named of these pairs. Where the apparatus is used to detect a ligand or analog of the ligand, the apparatus may further include a receptor which competes with the analyte ligand or analog for binding to the ligand on the monolayer. One exemplary ligand is an oligosaccharide ligand, and one exemplary receptor, the Verotoxin receptor, also known "Shiga-like toxin".

The electrode employed in the biosensor may be prepared, in accordance with another aspect of the invention, by (i) subjecting the conductive metal surface of the electrode substrate to mild oxidation conditions, (ii) adding to the substrate, a solution of hydrocarbon chains having lengths between 8–22 carbon atoms and derivatized at one chain end with a thiol group, and (iii) applying a positive potential to the electrode. The potential placed on the electrode is preferably at least 250 mV vs NHE (normal hydrogen electrode), in a solution containing the alkyl thiol to be deposited, and electrolytes including lithium ion and perchlorate anions. A selected portion of the hydrocarbon chains are derivatized at their ends opposite the thiol group, with the ligand of interest.

The oxidative conditions applied to the electrode surface are such as to produce deposition of a monolayer of close-packed, oriented chains on the substrate, as evidenced by the ability of the electrode to form an effective barrier to electron ion flow across the monolayer mediated by a redox ion species in an aqueous solution in contact with the monolayer.

In another general embodiment of the biosensor apparatus, ligand molecules are attached to the hydrocarbon chains forming the monolayer in the electrode through a heterodimer-subunit complex composed of first and second peptides that together form α-helical coiled-coil heterodimer, where: (i) the first peptide is covalently bound to the electrode surface through a spacer, such as an oligopeptide or hydrocarbon chain; (ii) the ligand is covalently attached to the second peptide; (iii) binding of the second peptide to the first peptide, to form such complex, is effective to measurably reduce the electron flow across the monolayer mediated by such redox ion species, relative to electron flow observed in the presence of the first peptide alone; and (iv) binding of a ligand-binding receptor to the ligand, with such forming part of said complex, is effective to measurably increase the electron flow across of the monolayer mediated by such redox species.

Also contemplated is an electrode for use in a biosensor apparatus of this type, composed of a substrate having a detection surface and ligand molecules attached to surface through an α-helical coiled-coil heterodimer of the type detailed above.

The electrode just described can be produced, in accordance with another aspect of the invention, by contacting together: (a) a detection surface having attached thereto, a first heterodimer-subunit peptide, and (b) a second heterodimer subunit capable of binding to the first subunit to form an α-helical heterodimer, and having a covalently attached ligand capable of binding specifically to such ligand-specific receptor.

These and other objects and features of the invention will become more fully apparent when the following detailed description of the invention is read in conjunction with the accompanying drawings.

BRIEF DESCRIPTION OF THE DRAWINGS

FIGS. 6A and 6B illustrate the perturbation of lipid monolayer structure with binding of PAK peptide to disaccharide ligands on a monolayer;

FIG. 7 shows plots of changes in oxidation (solid circles) and reduction (open squares) current of $Fe(CN)_6^{3-}/^{4-}$ as a function of time after addition of PAK peptide to the monolayer illustrated in FIGS. 6A and 6B;

FIGS. 17A–17E show a synthetic pathway used for producing a trisaccharide-hydrocarbon conjugate employed in the monolayer shown in FIGS. 8A–8C.

DETAILED DESCRIPTION OF THE INVENTION

Figure 1:
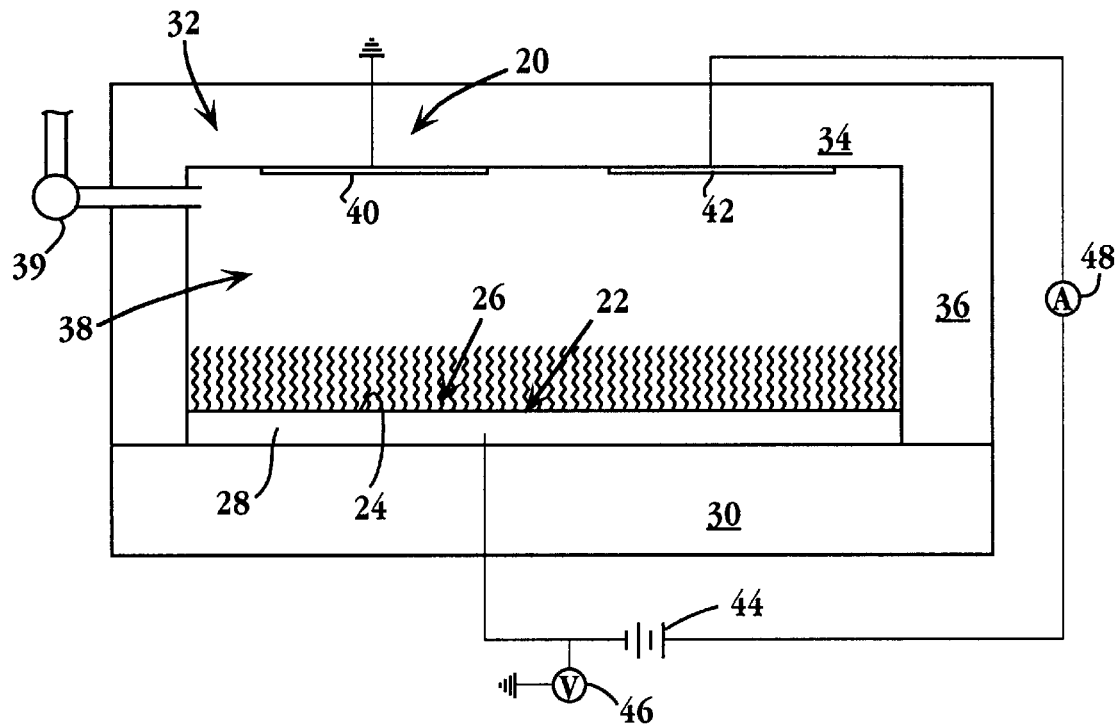
FIG. 1 is a simplified, partly schematic view of the a biosensor apparatus constructed in accordance with the invention.

A. Biosensor Apparatus FIG. 1 is a simplified schematic view of a biosensor apparatus 20 for detecting a binding event between a ligand and a ligand-binding receptor or agent, in accordance with the invention. The apparatus includes a working electrode 22 having a conductive detection surface 24, and a hydrocarbon-chain monolayer 26 formed on the detection surface. In the embodiment shown, the detection surface is the upper surface of a conductive film 28 deposited on an electrode substrate 30, which may be non-conductive material. Details of the monolayer formed on the detection surface, and the method of forming the monolayer on the surface, are discussed below.

A cover 32 in the apparatus has an upper wall 34, and side walls, such as wall 36, which are joined to edge regions of the electrode substrate to form a closed chamber 38 therewith. The chamber serves to hold an aqueous electrolyte solution required for biosensor operation, as will be described. Liquid may be introduced into or withdrawn from the chamber through a valved port 39 as shown. Although not shown, the chamber may include a second port or vent to facilitate liquid flow through the port.

A reference electrode 40 and a counter electrode 42 in the apparatus are carried on the chamber-facing surface of wall 34, as shown, and are thus both in conductive contact with electrode 22 when the chamber is filled with electrolyte solution. The reference electrode, which is held at ground, serves as the voltage potential reference of the working electrode, when a selected potential is placed on the working electrode by a voltage source 44. This potential is measured by a voltage measuring device 46 which may additionally include conventional circuitry for maintaining the potential at a selected voltage, typically between about −500 to +800 mV.

Voltage source 44 is connected to counter electrode 42 through a current measuring device 48 as shown, for measuring current flow between the two electrodes during biosensor operation. The reference and counter electrodes are Pt, Ag, Ag/AgCl, or other suitable electrodes. The reference and working electrodes, and the circuitry connecting them to the working electrode, are also referred to herein, collectively, as means for measuring ion-mediated electron flow across the working-electrode monolayer, in response to ligand-receptor binding events occurring at the monolayer surface.

Figure 2:
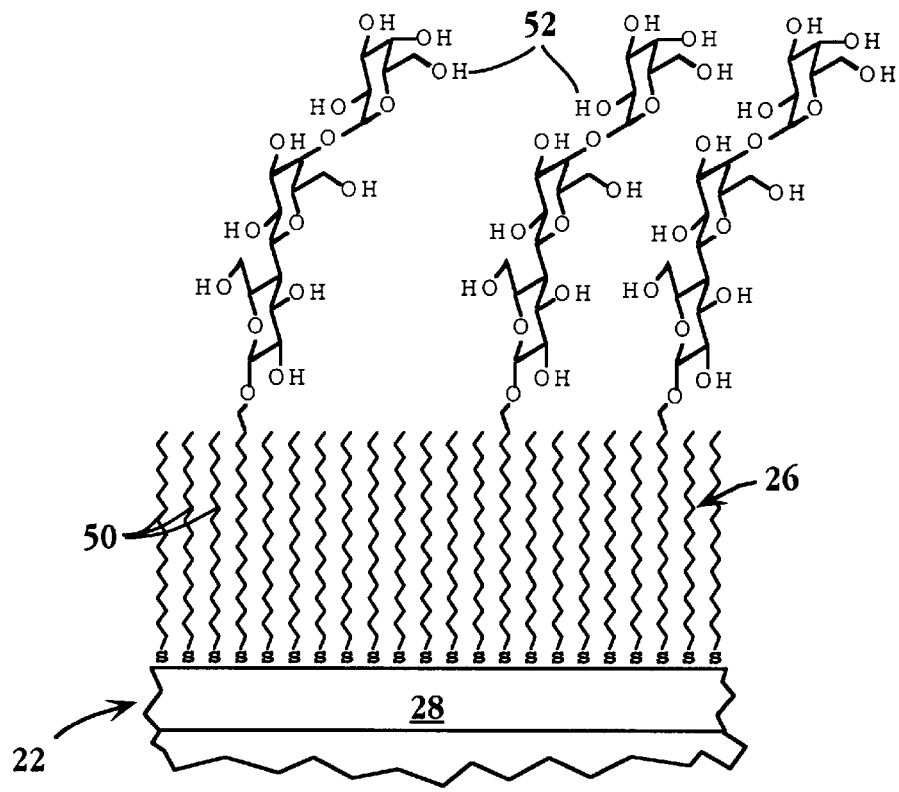
FIG. 2 is an enlarged view of a region the electrode in the biosensor shown in FIG. 1.

FIG. 2 is an enlarged view of a portion of the working electrode, including the electrode monolayer, showing individual hydrocarbon chains, such as chains 50, forming the monolayer, and ligand molecules, such as a trisaccharide ligand 52, covalently attached to distal ends of the hydrocarbon chains. The ligand employed in the biosensor is a selected binding partner in a ligand/receptor binding pair, where the analyte to be detected is related to one of the two binding partners. Ligand-receptor binding pairs used commonly in diagnostics include antigen-antibody, hormone-receptor, drug-receptor, cell surface antigen-lectin, biotin-avidin, and complementary nucleic acid strands, where the ligand is typically the smaller of the two binding pair members. The analyte to be detected may be either member of the binding pair, or alternatively, a ligand analog that competes with the ligand for binding to the complement receptor.

The ligand molecules are attached to distal ends of the chains through conventional derivatization reactions, e.g., ester, ether, amide, or sulfhydryl linkages, according to standard methods. The number of chains in the monolayer carrying distal-end ligands is preferably about 1 to 10 mole percent of the total chains, but may range from 0.01 to 100%.

The chains forming the monolayer are typically 8–22 carbon, saturated hydrocarbon chains, although longer chains, chains with some unsaturation, chains with non-carbon chain atoms, such as lipid ethers, and/or chains with minor branching, such as by non-chain methyl groups, may be employed, within the constraint that the chains, at a sufficient packing density, form a sufficiently close packed and ordered monolayer to be effective as a barrier to electron flow, under biosensor operating conditions, as discussed below. This density is calculated to be between 3–5 chains/$nm^2$.

Figure 13A:
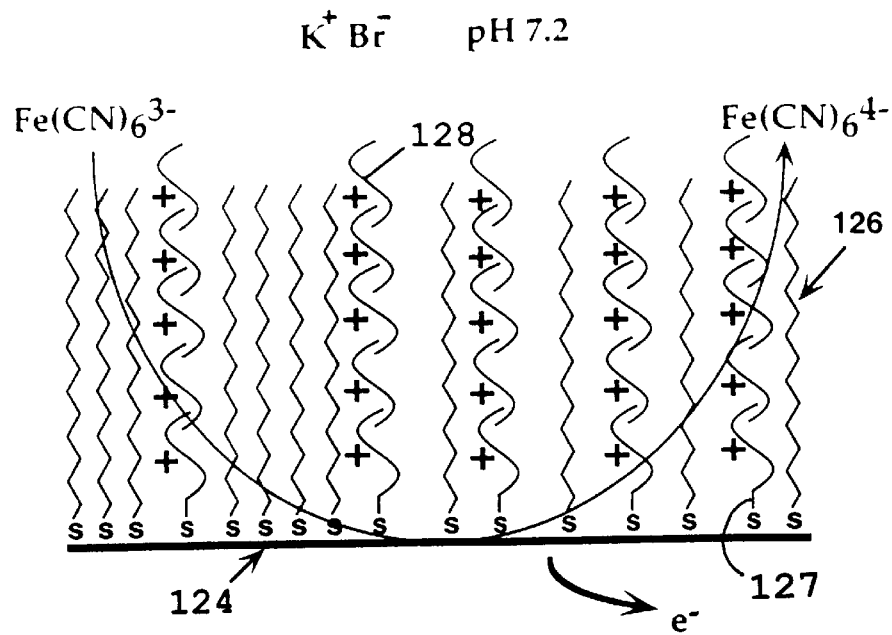
FIGS. 13A and 13B illustrate the structure of an electrode monolayer having an embedded K coil peptide subunit (13A), and an embedded K coil/E coil heteroduplex.
Figure 13B:
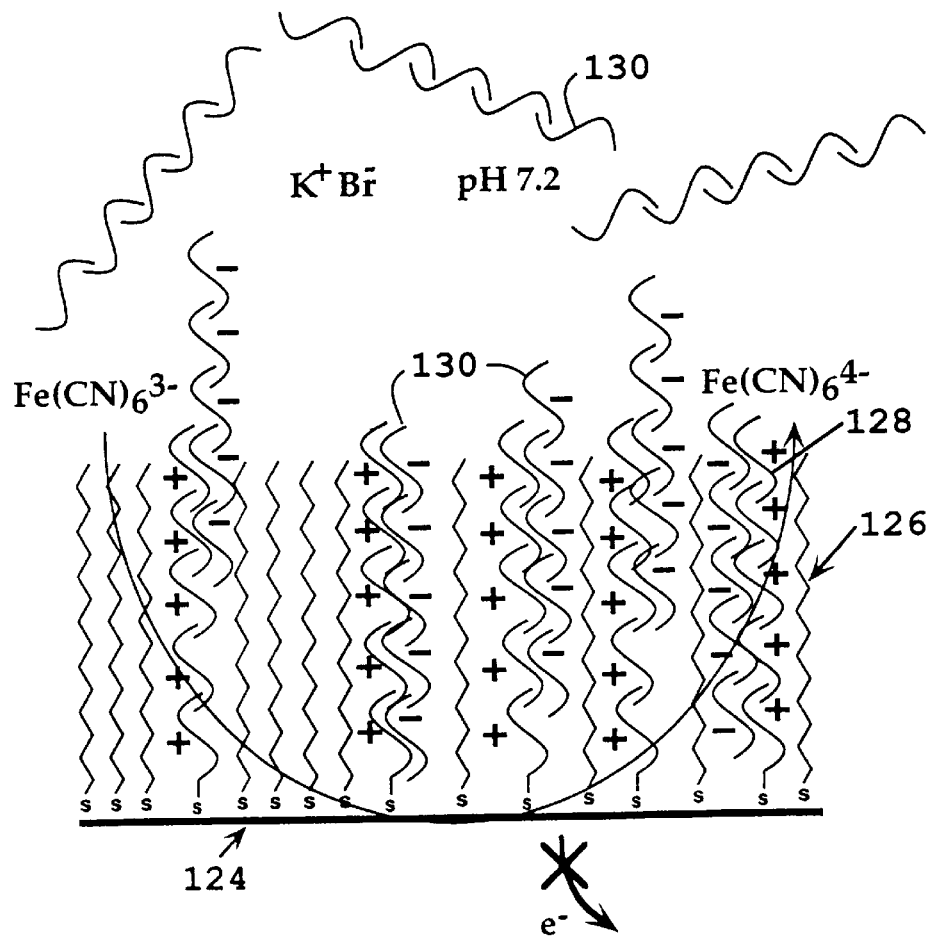
Figure 14:
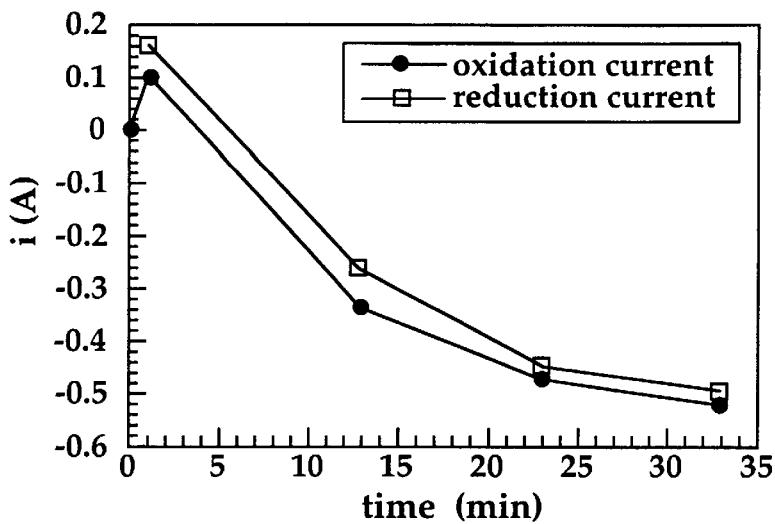
FIG. 14 shows the change in oxidation (solid circles) and reduction (open squares) current as a function of time after addition of E coil peptide subunit to an electrode of the type illustrated in FIG. 13A containing an embedded K coil peptide subunit.
Figure 15:
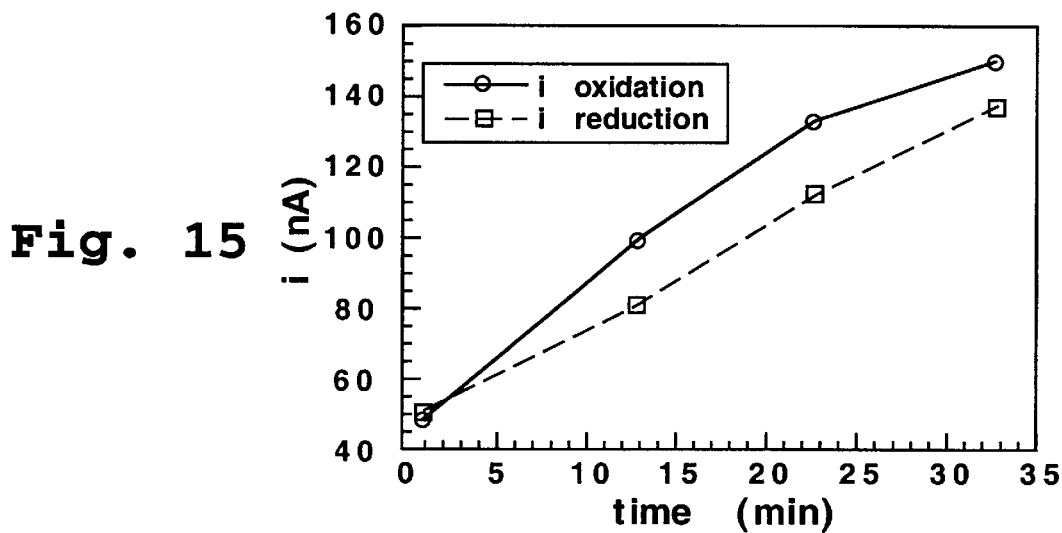
FIG. 15 shows changes in oxidation of $Fe(CN)_6^{3-}/^{4-}$ (open circles) and reduction (open squares) as a function of time after addition of PAK peptide to an electrode containing di-saccharide ligands on a K coil/E coil lipid monolayer.
Figure 16:
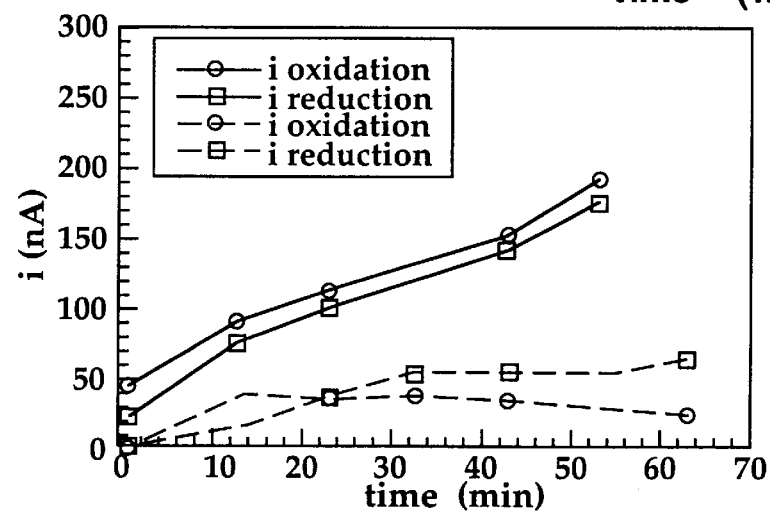
FIG. 16 shows changes in oxidation of $Fe(CN)_6^{3-}/^{4-}$ (open circles) and reduction (open squares) as a function of time after addition of Verotoxin peptide to an electrode containing trisaccharide ligands on a K coil/E coil lipid monolayer.
Figure 17E:
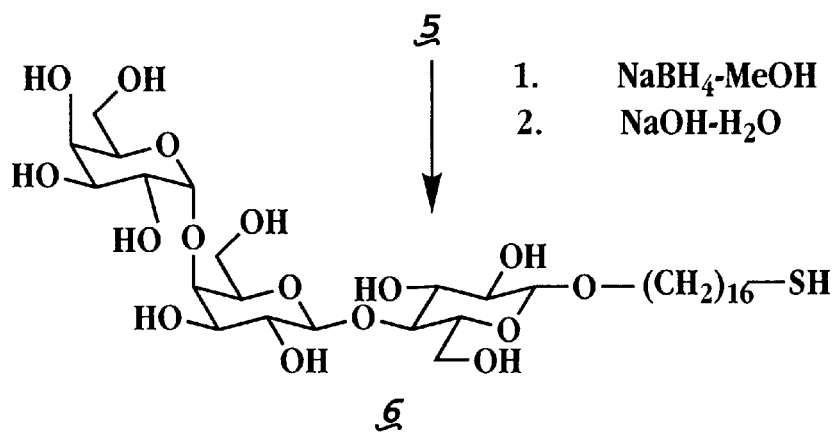
Figure 18:
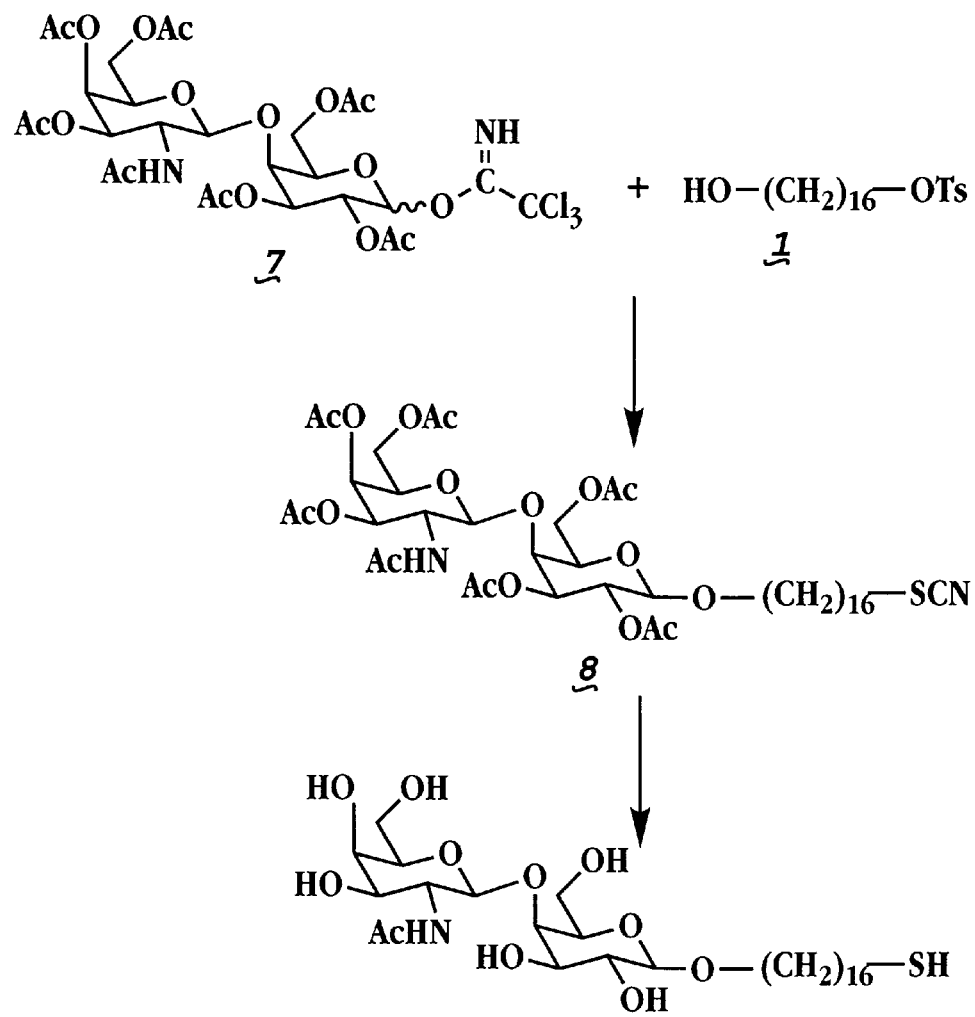
FIG. 18 shows a synthetic pathway used in producing a disaccharide-hydrocarbon conjugate employed in the monolayer shown in FIGS. 6A and 6B.

As an example of the variation in chain composition allowed, the embodiment of the invention shown in FIG. 13B has a hydrocarbon-chain monolayer that includes coil—coil peptide heterodimers embedded in the planar chain matrix, while still retaining a low dielectric barrier to ion flow through the monolayer.

In the embodiment shown, the chains are coupled to the electrode detecting surface through sulfhydryl linkages, although other suitable coupling groups may be employed. Methods for producing monolayers having suitable hydrocarbon chain densities will now be discussed.

B. Electrode Monolayer Production FIGS. 3A–3C illustrate three methods for forming hydrocarbon chain monolayers suitable for use in the biosensor electrodes.

Figure 3A:
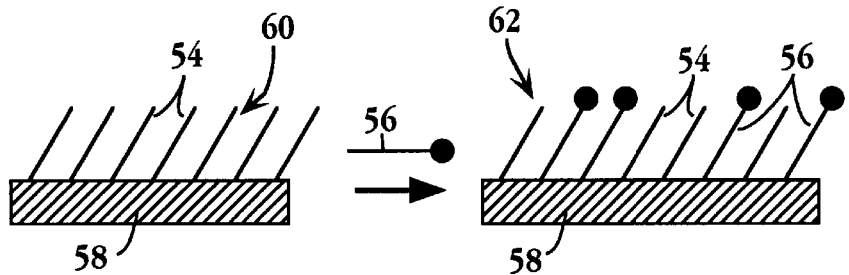
FIGS. 3A–3C illustrate three methods for forming a biosensor electrode having a lipid monolayer and attached ligand molecules, in accordance with the invention.
Figure 3B:
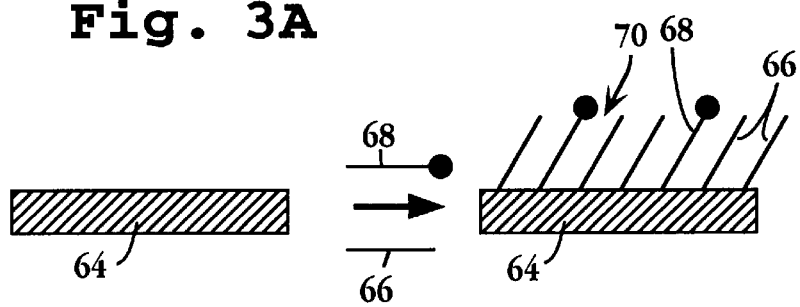
Figure 3C:
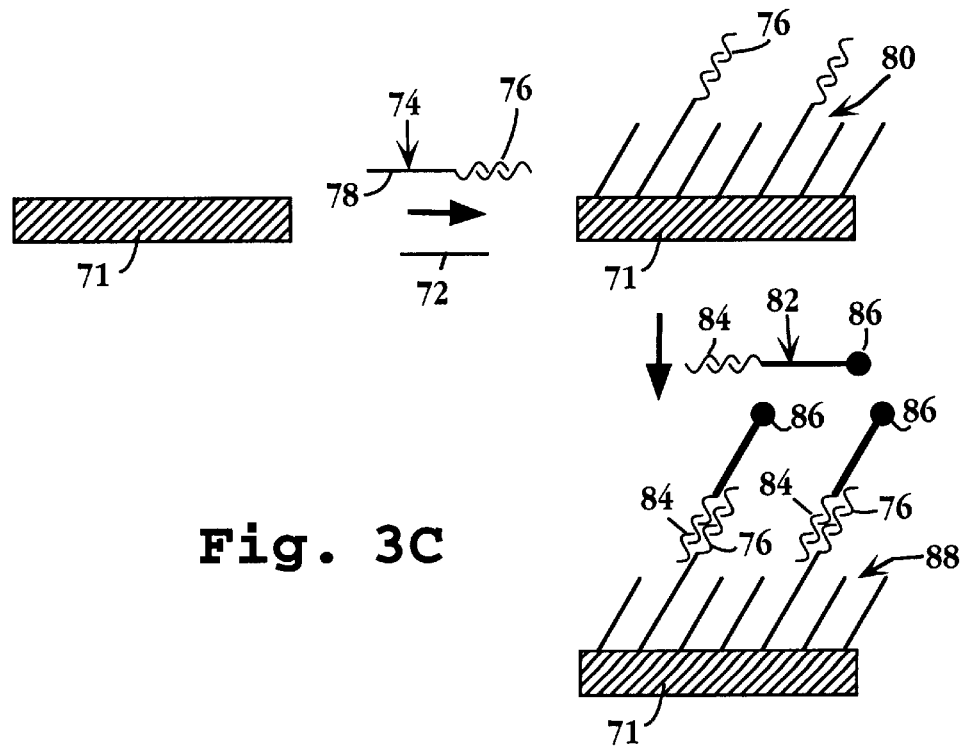

One approach, illustrated in FIG. 3A, involves passive diffusion of chains, such as hydrocarbon chains 54 and ligand-derivatized chains, such as chains 56, onto the surface an electrode 58, under conditions effective to couple the diffused chains to the electrode detection surface. The diffusion method illustrated in 3A is a two-step process. In the first step, hydrocarbon chains alone (in the absence of ligand-derivatized chains) are allowed to react with the detected surface over an extended period, e.g., 24–48 hours, until a selected packing density less than full packing density is achieved.

The diffusion reaction is carried out under conditions suitable for coupling the derivatized chains to the detection surface. Where the chains have thiol coupling groups, and the electrode surface is gold, the surface is subjected to mild electro-chemically oxidizing conditions, with a perchlorate salt present in solution, then reacted with the chains under mildly oxidizing conditions.

The extent of packing can be monitored, for example, by ellipsometry measurements to determine the thickness of the layer on the detection surface. At maximum density, i.e., saturation, a given chain length will produce a given monolayer thickness. As a guide, $C_{22}$ chains produce a maximum monolayer thickness of about 30 Å, and shorter length chains, proportionately thinner monolayers. Thus, in the case of a monolayer formed of $C_{22}$ chains, the passive buildup of the monolayer may be stopped when a 25 Å monolayer thickness is observed.

The second diffusion step involves the passive diffusion of ligand-derivatized chain 56 onto the partially formed monolayer, indicated at 60, again under suitable thiolate coupling conditions, until a high-density monolayer 62 is achieved, as evidenced, for example, by the measured thickness of the monolayer and/or a plateauing of the thickness/time curve.

Although this approach has been applied successfully to monolayer production in the invention, 35 it suffers from two limitations. First, rather long diffusion times—on the order of one to several days—are required to reach maximum packing density. Secondly, the percent chains containing attached ligands is difficult to control reproducibly, so that the final monolayers will have variable mole percentages of ligands, and thus, different performance characteristics.

These limitations are substantially overcome in the method illustrated in FIG. 3B, in accordance with another novel aspect of the invention. In this approach, a mixture of free and ligand-carrying hydrocarbon chains, such as chains 66, 68, respectively, at a desired mole ratio, are actively driven to the surface by applying a positive voltage potential to the substrate, here indicated at 64. In practice, the hydrocarbon chain mixture (about 1 mM hydrocarbon chains) in an ethanolic solution of 100 mM Li perchlorate, neutral pH, is added placed over the electrode, and a selected potential is applied to the electrode. The buildup of the monolayer can be monitored by increase in layer thickness, as above. Preferably, however, monolayer formation is monitored by measuring electron flow across the monolayer, e.g., employing the circuit configuration shown in FIG. 1. In this case, formation of the monolayer, indicated at 70, will be characterized by a steady drop in electrode current, until a stable low current flow is reached, at which point maximum chain packing has been achieved.

Figure 4:
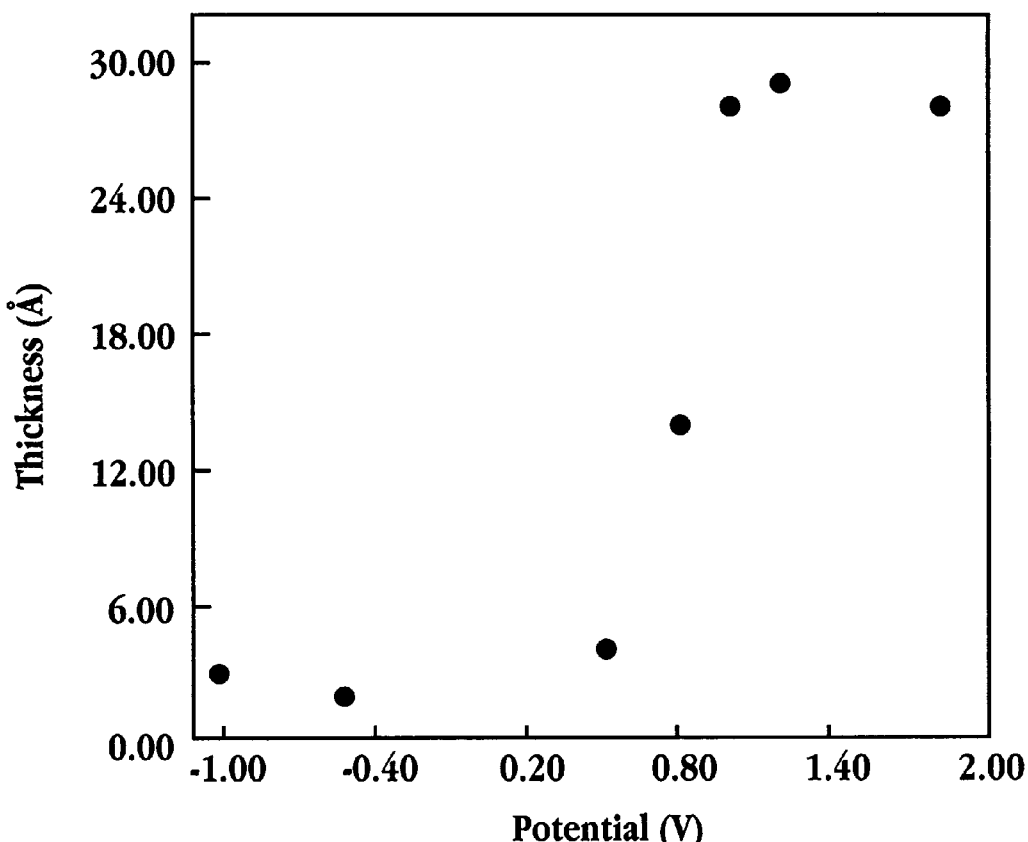
FIG. 4. is a plot of monolayer thickness as a function of applied voltage in an electrode monolayer formed in accordance with the method illustrated in FIG. 3B.

The time required to achieve saturation packing density will vary with applied voltage, and can be a short as 10 seconds—that is, about 4 orders of magnitude faster than monolayer formation by diffusion. FIG. 4 is a plot of monolayer thickness formed using a thiol-group $C_{22}$ hydrocarbon chain under coupling conditions like those above, after 10 minutes at the electrode voltage indicated. As seen, complete or nearly complete monolayer formation (30 Å thickness) occurs within 10 minutes at about 1V (vs. NHE) potential and above. At lower positive voltages, additional reaction time is required. Preferably the voltage applied to the electrode is at least voltage between about +250 mV relative to a normal hydrogen electrode (+250 mV vs. NHE) and 1.2V (vs. NHE).

Not only are rapid monolayer formation times achieved, but the percentages of ligand- and non-ligand chains present in the reaction mixture are precisely represented in the monolayers, giving highly reproducible electrode characteristics.

FIG. 3C shows a modification of the FIG. 3B method, where the hydrocarbon-chain mixture reacted with the electrode (indicated at 71) includes non-ligand chains, such as chains 72, and peptide subunit conjugates, such as indicated at 74, containing a peptide subunit 76 that is capable of forming a stabilized, alpha-helical peptide heterodimer with an oppositely charged, complementary subunit. Such heterodimer subunits are described in PCT patent application WO 95/31480, for "Heterodimer Polypeptide Immunogen Carrier Composition and Method", publication date Nov. 23, 1995, which is incorporated herein by reference. Exemplary subunits are referred to herein as K coils, referring to a positively charged subunits whose charge is provided dominantly by lysine residues, and E coils, referring to negatively charged subunits whose charge is provided dominantly by glutamic acid residues.

In the embodiment shown, subunit 76 is attached to the distal end of a hydrocarbon chain 78 (end opposite the chain's thiol group) by suitable lipid-to-peptide conjugation, e.g., by ester linkage to a hydrocarbon fatty acid. Alternatively, and as described below, the peptide subunit may be linked to the electrode surface through a peptide spacer, e.g., tripeptide spacer that extends from one end of the subunit and includes cysteine as a terminal residue, for sulfhydryl attachment to the electrode surface. In both cases, the peptide subunit conjugate is mixed with the hydrocarbon chains, at a selected mole ratio, then driven into a monolayer formation by applying a positive voltage to the electrode, as above, until a densely packed monolayer 80 is formed.

A suitable ligand is then attached to the monolayer by contacting the monolayer with a ligand-coil conjugate 82 composed of the oppositely charged complement of the monolayer coil, indicated at 84, coupled to a selected ligand 86. The two oppositely charged subunits spontaneously self-assemble into heterodimers, effectively coupling the ligand to the monolayers with the high affinity constant of the two heterodimers.

The method provides, in addition to the advantages mentioned above with respect to FIG. 3B, a "universal" biosensor substrate which can be modified to include one of a large number of different ligands in the substrate monolayer, simply by contacting the universal substrate with a conjugate of the oppositely charged peptide subunit and the selected ligand. In the example shown in FIG. 3C, a densely packed monolayer 80 is converted to a ligand-specific monolayer 88 by addition of the ligand-specific conjugate 82.

C. Biosensor Characteristics: Directly Attached Ligand

This section examines the dielectric properties of the biosensors of the invention, as evidenced by the conductance properties of the biosensor monolayer membranes in the presence and absence of ligand-receptor binding. The present section considers membranes having directly attached ligands of the type described with respect to FIGS. 3A and 3B. The next section examines similar electrical properties in biosensor membranes in which the ligand is attached through heterodimer peptide subunits, as described with respect to FIG. 3C.

Figure 5:
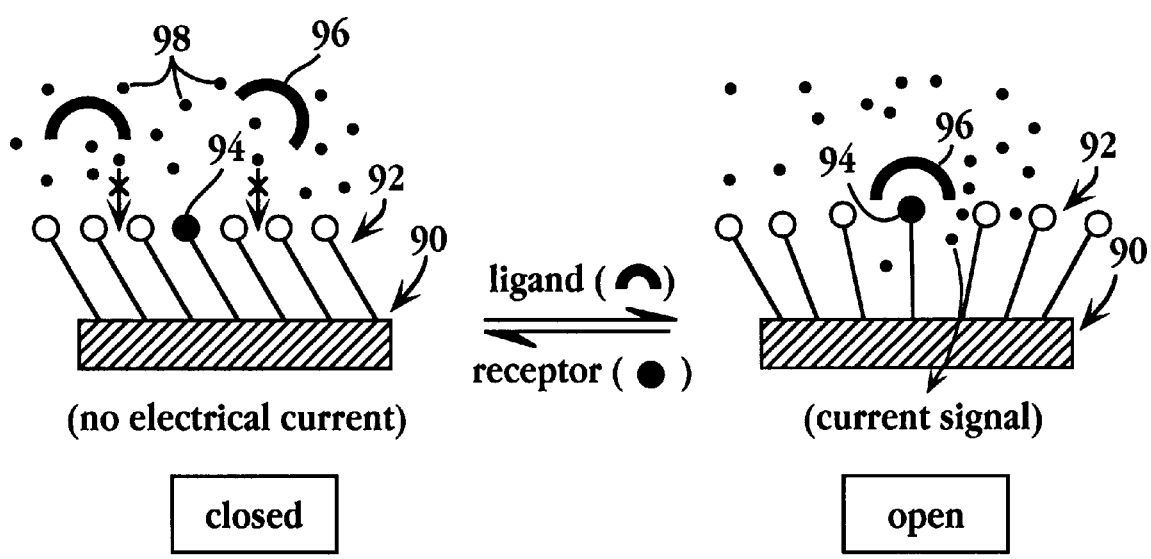
FIG. 5 illustrates the triggering of conductance by receptor-ligand interaction on a biosensor electrode, in accordance with the invention.

The basic operational features of the biosensor are illustrated in FIG. 5. The figure shows a biosensor electrode 90 in a biosensor apparatus of the type described in FIG. 1, where an electrode monolayer 92 is formed, as above, of a densely ordered array of hydrocarbon chains containing ligand molecules, such as molecule 94, attached to the distal ends of some of the chains.

The electrode is in contact with a solution of ionic species, indicated at 98, capable of undergoing a redox reaction, i.e., losing or gaining an electron, at a suitably charged electrode. Exemplary redox species are $Fe(CN)_6^{3-/4-}$, as a negatively charged species, and $Ru(NH_3)_6^{2+/3+}$ as a positively charged species. Other probes which can be used include $Mo(CN)_6^{3-}$ ($E_0$=+800 mV), $W(CN)_6^{3-}$ ($E_0$=+580 mV), $Fe(CN)_4^-$ ($E_0$=+580 mV), $Ce^{4+/3+}$, ($E_0$=+1.4V), and $Fe^{+3/2+}$ ($E_0$=+666 mV). Typical redox ion concentrations are between 0.01 and 10 mM. The redox solution is contained in a chamber, like chamber 38 in FIG. 1, and is in contact with reference and counter electrodes.

The voltage potential placed on the electrode, i.e., between the electrode and reference electrode, is typically at least 90 mV above the electrochemical potential ($e_0$) value of the redox species, for oxidation, and at least 90 mV below the electrochemical potential, for reduction of the species. Consider, for example, $Fe(CN)_6^{3-/4-}$ with an $E_0$ of 450 mV (vs. NHE). Above about 550 mV electrode potential, any Fe2+ species is oxidized to Fe3+, and at an electrode potential below about 350 mV, and Fe+3 is reduced to Fe+2. Similarly, $Ru(NH_3)_6^{2+/3+}$ has an $E_0$ of +50 mV (vs. NHE), so oxidation is achieved at an electrode potential above about +150 mV, and reduction, below about –50 mV.

In the absence of receptor binding to the ligand, the monolayer retains its dense ordered packing, forming an effective barrier to electron flow across the monolayer mediated by the redox ion species, when a suitable oxidizing or reducing potential is placed across the monolayer. This is reflected by a low or zero measured current across the membrane. The dielectric constant of the monolayer in this condition is typically about 1–2.

With binding of a receptor 96 to a ligand on a monolayer, as shown at the right in the figure, the ordered structure of the monolayer is perturbed sufficiently to allow the movement of redox species through the monolayer, producing electron flow through the electrode. Measurements performed in support of the invention indicate that one triggering event leads to 102 to 106 ionic and electron transfer events per second, and thus is highly multiplicative. The biosensor records this binding event as an increase in current across the electrode, i.e., between the working and counter electrodes.

By analogy to a transistor, the redox solution serves as the "source", the monolayer as the "gate", and the underlying electrode as the "drain". Current flow in a transistor is initiated by applying a threshold voltage to the gate. In the biosensor of the invention, current flow is initiated by a stimulus—in this case, a ligand-receptor binding event—to the monolayer "gate".

A biosensor electrode 100 constructed in accordance with the invention, and having a disaccharide ligand indicated at 102 is shown before and after receptor binding in FIGS. 6A and 6B, respectively. Synthesis of the disaccharide-hydrocarbon chain used in the membrane is described in Examples 1D and 1E. The electrode was prepared as described with reference to FIG. 3B, employing a ratio of non-ligand to ligand-chains of about 4 to 1. The disaccharide is specifically reactive with a Pseudomonas PAK peptide, indicated at 104, forming a ligand-receptor pair with the peptide.

The increase in biosensor electrode current, when PAK peptide receptor is added to the biosensor chamber, is seen in FIG. 7 for both oxidation (solid circles) and reduction (open squares) current from $Fe(CN)_6^{3-/4-}$. The increase over time presumably reflects the kinetics of binding, demonstrating that the biosensor is useful as well in measuring the rate ligand-receptor binding events. FIG. 6B illustrates the perturbation of the hydrocarbon chain structure with receptor binding.

Figure 8A:
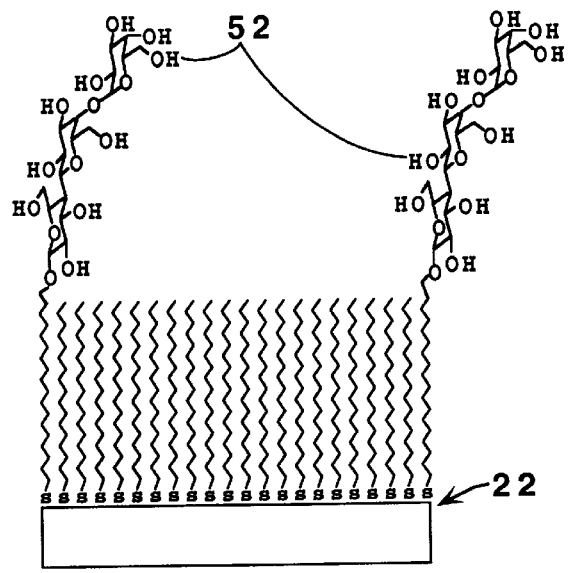
FIGS. 8A–8C illustrate the perturbation of lipid monolayer structure with binding of Verotoxin to trisaccharide ligands on a monolayer.
Figures 8B, 8C:
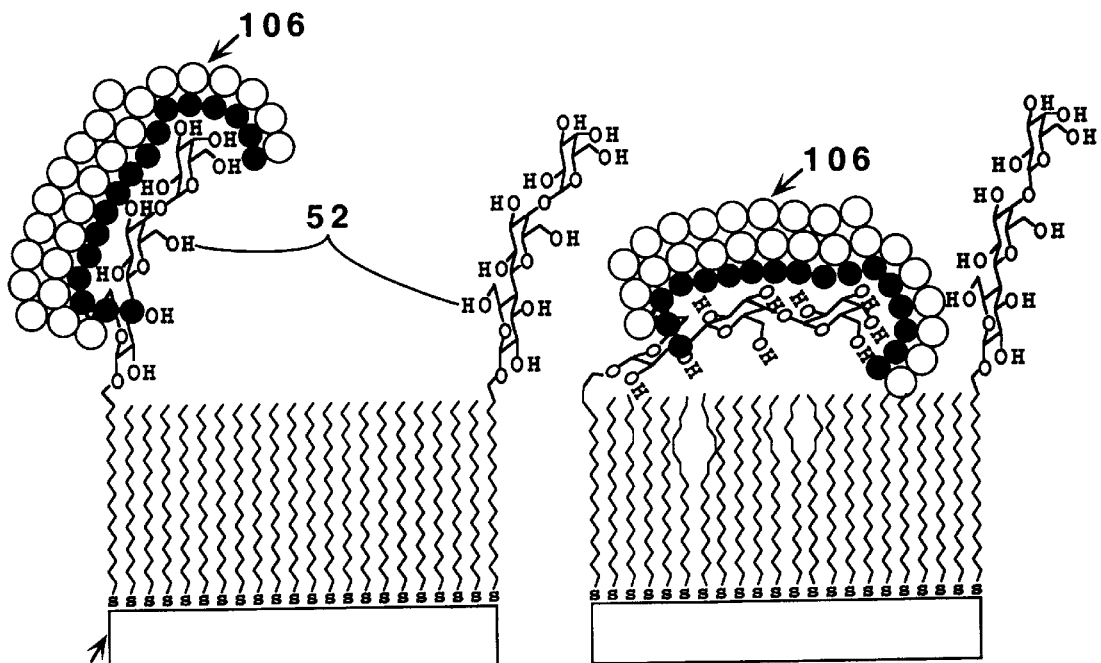

As another example, the biosensor electrode illustrated in FIGS. 8A–8C (electrode 22 from FIG. 2) has a trisaccharide ligand 52 which is shown before and after receptor binding in FIG. 6A and FIGS. 6B and 6C, respectively. Synthesis of the trisaccharide-hydrocarbon chain used in the membrane is described in Examples 1B and 1C. The electrode was prepared as described with reference to FIG. 3B, employing a ratio of non-ligand to ligand-chains of about 4 to 1. The disaccharide is specifically reactive with a Verotoxin, indicated at 106, forming a ligand-receptor pair. Verotoxin was prepared as described in Example 2.

FIGS. 8B and 8C illustrate two possible binding configurations. The configuration in FIG. 8B has little effect on the monolayer structure, and hence on biosensor current, because binding is "remote" from the membrane surface; the configuration illustrated in FIG. 8C, by contrast, produces significant perturbation of the monolayer structure, and thus would be expected to significantly enhance biosensor current.

Figure 9:
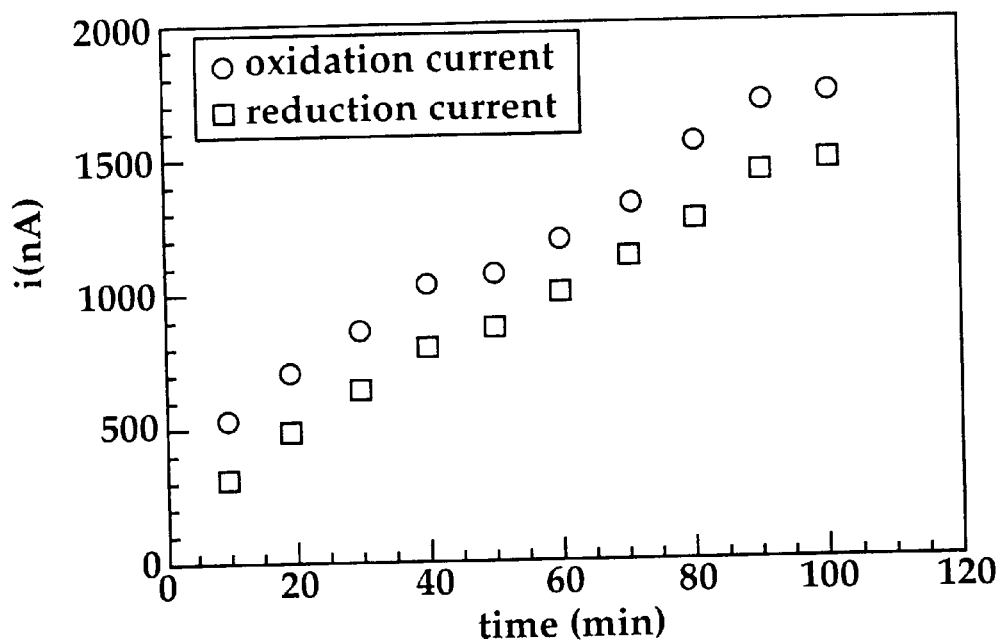
FIG. 9 shows plots of changes in oxidation (solid circles) and reduction (open squares) current of $Fe(CN)_6^{3-}/^{4-}$ as a function of time after addition of Verotoxin to the monolayer illustrated in FIGS. 8A and 8B.

The oxidation and reduction current plots shown in FIG. 9 demonstrate that Verotoxin binding to the membrane does in fact produce a major change in monolayer structure. As seen, both oxidation and reduction current increase from near-zero levels, in the absence of Verotoxin, to a level in the $\mu$Amp range an hour after Verotoxin is introduced into the biosensor.

In the examples above, the stimulation of biosensor current by receptor binding may be the result of (i) steric perturbation of the monolayer chains, as indicated in FIGS. 6B and 8C, (ii) charge effects on the monolayer surface due to charged groups on the receptor, or (iii) a combination of the both effects. Studies conducted in support of the invention indicate that both effects can be operative.

Figure 10:
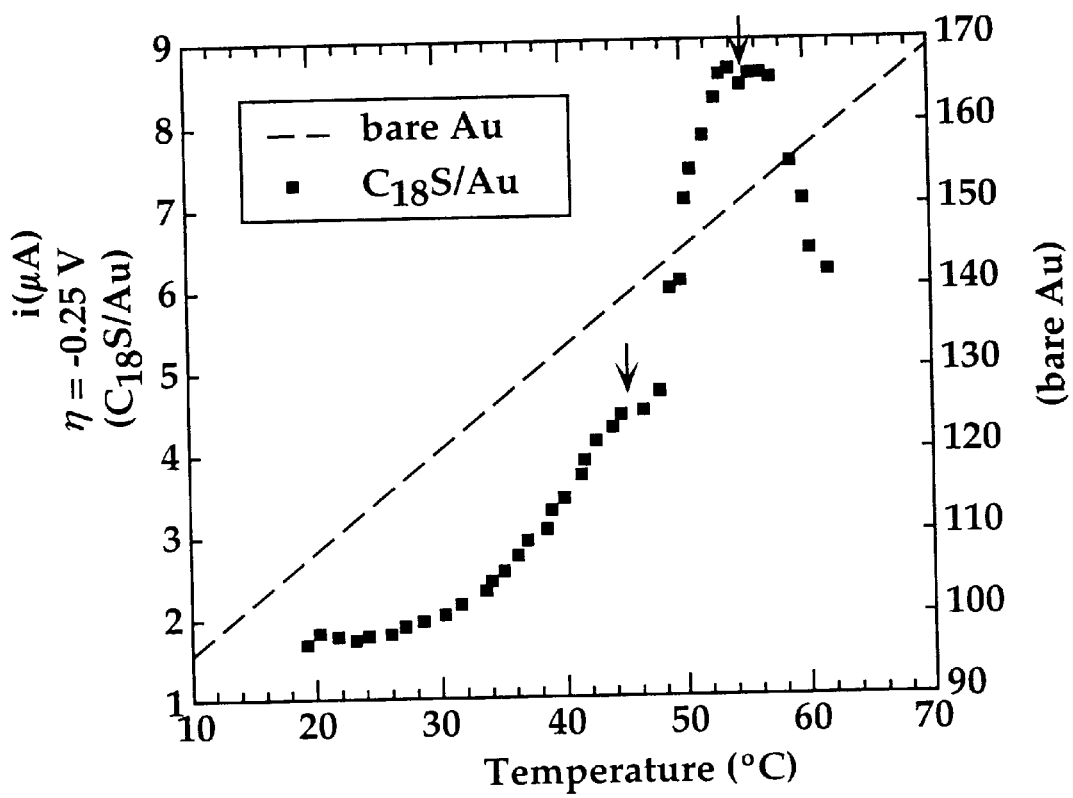
FIG. 10 is a plot of electrode current of $Fe(CN)_6^{3-}/^{4-}$ as a function of temperature in a monolayer electrode constructed in accordance with the invention.

The effect of hydrocarbon-chain disruption in the biosensor monolayer, was examined by plotting biosensor current as a function of electrode temperature. If lipid-chain disruption leads to greater electron flow in the biosensor, raising the temperature of the monolayer, and thus the motion of the lipid chains, should increase measured electron flow mediated by redox carriers. This was in fact observed, as seen in FIG. 10. The current/temperature plot has a peak corresponding to the phase transition temperature of the monolayer chains (about 55° C.), consistent with the idea that maximum lipid disruption occurs at the point of maximum extent of phase boundaries in the hydrocarbon chains.

The effect on conductance of charge on the monolayer surface can be seen from FIGS. 11A–11B and 12A–12B. In the study represented in FIG. 11A, a negatively charged ligand was attached to the distal ends of a portion of the chains forming the monolayer. In the figure, the electrode is indicated at 108, the monolayer, at 110, chains forming the monolayer, at 112, and chain-attached ligands, at 114. Electrode current was measured for the negatively charged redox species $Fe(CN)_6^{3-/4-}$, and independently, with the positively charged species $Ru(NH_3)_6^{2+/3+}$, at oxidation potentials indicated above.

Figures 11A, 11B:
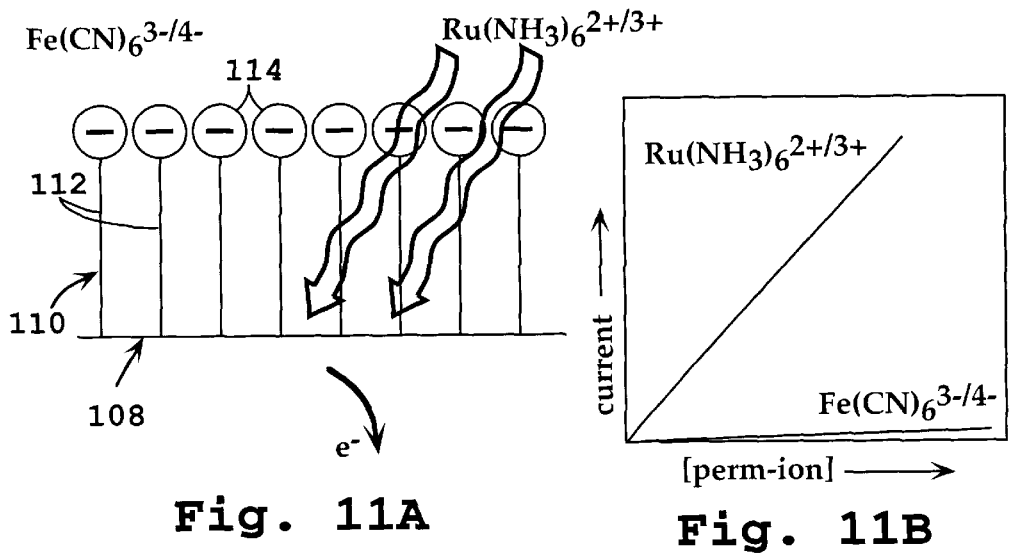
FIGS. 11A and 11B demonstrate ion gating effects with a negatively charged ligand in an electrode monolayer.

As seen in FIG. 11B, the oxidation current for the positively charged species shows the ion-dependent behavior expected for ion migration through the monolayer, indicating that the monolayer is conductive to positively charged redox species. Conversely, no significant electron flow was observed with the negatively charged redox species.

Figures 12A, 12B:
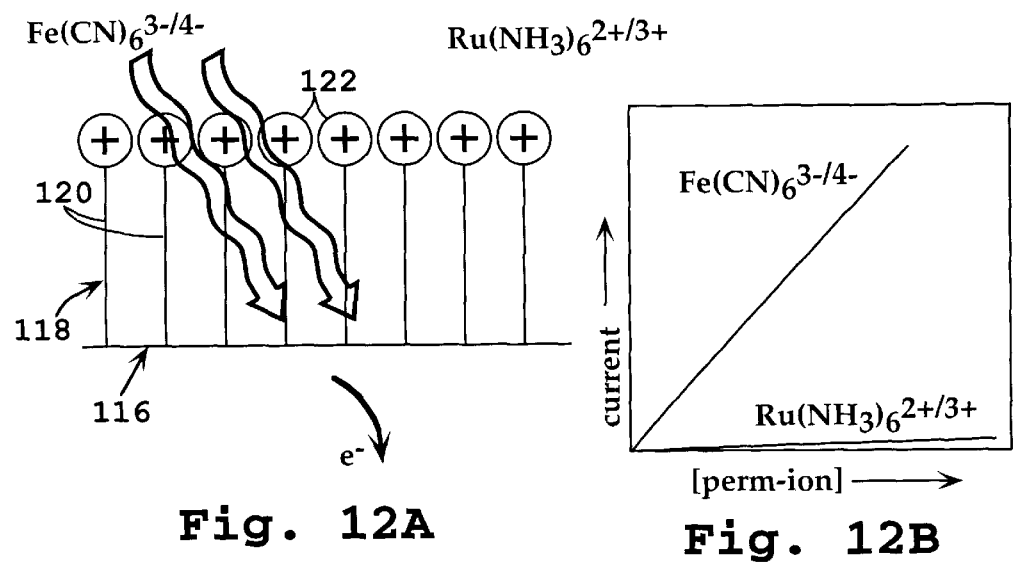
FIGS. 12A and 12B demonstrate ion gating effects with a positively charged ligand in an electrode monolayer.

Similar results were obtained with a monolayer designed to contain a positively charged surface ligand, as illustrated in FIG. 12A. In this figure, the electrode is indicated at 116, the monolayer, at 118, chains forming the monolayer, at 120, and chain-attached ligands, at 122. As seen in FIG. 12B dependent current was observed for oxidation of the negatively charged iron redox species, but not the positively charged ruthenium species.

D. Biosensor Characteristics: Heterodimer Attached Ligand

In another embodiment, the ligand in the biosensor is anchored to biosensor surface, i.e., embedded within the hydrocarbon-chain monolayer, by a coiled-coil heterodimer complex formed of two subunit peptides. The heterodimer-subunit peptides employed in the biosensor invention are two non-identical, preferably oppositely charged polypeptide chains, typically each about 21 to about 70 residues in length, having an amino acid sequence compatible with their formation into two-stranded α-helical heterodimeric coiled-coils. They are designated herein as HSP1 (heterodimer-subunit peptide 1), and HSP2 (heterodimer-subunit peptide 2). In the discussion below, HSP1 will refer to the peptide attached to the biosensor surface in the biosensor, and HSP2, to the peptide having an attached ligand. It will be understood that these designations refer to the functional role played by the subunit peptide, not the actual peptide sequence.

In aqueous medium, the isolated heterodimer-subunit peptides are typically random coils. When HSP1 and HSP2 are mixed together under conditions favoring the formation of α-helical coiled-coil heterodimers, they interact to form a two-subunit α-helical coiled-coil heterodimeric complex.

Peptides in an α-helical coiled-coil conformation interact with one another in a characteristic manner that is determined by the primary sequence of each peptide: The tertiary structure of an α-helix is such that 7 amino acid residues in the primary sequence correspond to approximately 2 turns of the α-helix. Accordingly, a primary amino acid sequence giving rise to an α-helical conformation may be broken down into units of 7 residues each, termed heptads. The heterodimer-subunit peptides are composed of a series of heptads in tandem. When the sequence of a heptad is repeated in a particular heterodimer-subunit peptide, the heptad may be referred to as a "heptad repeat", or simply "repeat".

Specific types of amino acid residues at defined positions in each heptad act to stabilize the two-stranded α-helical coiled-coil heterodimeric structure or complex. The heterodimer peptides may also contain residues that can be reacted (either intra- or inter-helically) to stabilize the α-helical or coiled-coil nature of the polypeptides. One example of a stabilizing modification is the incorporation of lactam bridges in the first and last (terminal) repeats of heterodimer-subunit peptides, as detailed in PCT application WO 95/31480 for "Heterodimer Polypeptide Immunogen Carrier Composition and Method", publication date Nov. 23, 1995, which is incorporated herein by reference.

The dimerization of HSP1 and HSP2 is due to the presence of a repeated heptad motif of conserved amino acid residues in each peptide's primary amino acid sequence. Repeating heptad motifs having appropriate amino acid sequences direct the HSP1 and HSP2 polypeptides to assemble into a heterodimeric α-helical coiled-coil structure under permissible conditions. The individual α-helical peptides contact one another along their respective hydrophobic faces.

HSP1 and HSP2 may assemble into a heterodimer coiled-coil helix (coiled-coil heterodimer) in either parallel or antiparallel configurations. In a parallel configuration, the two heterodimer-subunit peptide helixes are aligned such that they have the same orientation (amino-terminal to carboxyl-terminal). In an antiparallel configuration, the helixes are arranged such that the amino-terminal end of one helix is aligned with the carboxyl-terminal end of the other helix, and vice versa.

Heterodimer-subunit peptides designed in accord with the guidance presented in the above PCT application typically show a preference for assembling in a parallel orientation vs. an antiparallel orientation. For example, the exemplary peptides identified by SEQ ID NO:1 and SEQ ID NO:2 form parallel-configuration heterodimers as do other peptide sequences discussed in the PCT application. When attaching a ligand to HSP2, it is generally desirable to attach the ligand at or near the end of the peptide that will form the distal end of the heterodimer. In particular, where the heterodimer forms a parallel configuration, the HSP1 peptide is preferably anchored to the biosensor surface at its C terminus, and the ligand attached to the HSP2 peptide at its N terminus.

As just noted, one of the two subunit peptides (HSP1) in the heterodimer is attached to the biosensor surface, and the second peptide (HSP2) contains a ligand intended to participate in an analyte-dependent ligand/anti-ligand binding reaction. In both cases, the peptide is synthesized, or derivatized after synthesis, to provide the requisite attachment function and ligand, respectively.

Considering the modification of HSP1, the peptide may be synthesized, at either its N or C terminus, to carry additional terminal peptides that can function as a spacer between the biosensor surface and the helical-forming part of the peptide. Alternatively, the HSP1 peptide can be attached to the biosensor surface thorough a high-affinity binding reaction, such as between a biotin moiety carried on the peptide and an avidin molecule covalently attached to the surface.

Where the heterodimer is embedded in a hydrocarbon-chain monolayer, as described below, the spacer anchoring the HSP1 peptide to the biosensor surface may be a hydrocarbon chain. The chain is preferably a fractional length of the chains making up the bilayer, such that the distal ends of the heterodimer peptides in the assembled monolayer are at or near the exposed surface of the monolayer. Thus, for example, if the monolayer is made up of 18-carbon chains, the spacer is preferably 2–10 carbons in length, depending on the length of the assembled heterodimer.

The hydrocarbon-chain spacer, in the form of a omega-thio fatty acid, may be coupled to a terminal hydroxyl or amine coupling during solid-phase synthesis, as outlined above. The derivatized peptide, in turn, can be attached to a metal surface by standard thiolate coupling (Dakkouri, et al., Langmuir (1996) 12:2849–2852).

Considering the ligand-attachment to HSP2, the ligand selected will be determined by the analyte to be tested.

Ligand-receptor binding pairs, i.e., ligand/ligand-binding agent pairs used commonly in diagnostics include antigen-antibody, hormone-receptor, drug-receptor, cell surface antigen-lectin, biotin-avidin, substrate/enzyme, and complementary nucleic acid strands. The ligand is typically the smaller of the two binding pair members, particularly where the ligand is attached to a hydrocarbon-chain monolayer, as described below. However, attachment of either binding pair is contemplated herein.

Where the ligand is a polypeptide, e.g., peptide antigen, the antigen can be synthesized by either solid-state or recombinant methods, to include the peptide antigen at the end of the HSP2 peptide that will orient distally in the assembled heterodimer. Where the ligand is a non-peptide moiety, e.g., a non-peptide hormone, drug, or nucleic acid, the HSP2 peptide can be synthesized to include one or more residues that can be specifically derivatized with the ligand. The ligand is preferably covalently attached to the N-terminal amino acid residue, or to one or the residues facing the exposed face of the heterodimer. Preferred coupling groups are the thiol groups of cysteine residues, which are easily modified by standard methods. Other useful coupling groups include the thioester of methionine, the imidazolyl group of histidine, the guanidinyl group of arginine, the phenolic group of tyrosine and the indolyl group of tryptophan. These coupling groups can be derivatized using reaction conditions known to those skilled in the art.

To attach the ligand-derivatized HSP2 peptide to the surface-immobilized HSP1 peptide, the two peptides are contacted under conditions that favor heterodimer formation. A medium favoring coiled-coil heterodimer formation is a physiologically-compatible aqueous solution typically having a pH of between about 6 and about 8 and a salt concentration of between about 50 mM and about 500 mM. Preferably, the salt concentration is between about 100 mM and about 200 mM. An exemplary benign medium has the following composition: 50 mM potasisium phosphate, 100 mM KCl, pH 7. Equally effective media may be made by substituting, for example, sodium phosphate for potassium phosphate and/or NaCl for KCl. Heterodimers may form under conditions outside the above pH and salt range, medium, but some of the molecular interactions and relative stability of heterodimers vs. homodimers may differ from characteristics detailed above. For example, ionic interactions between the ionic groups that tend to stabilize heterodimers may break down at low or high pH values due to the protonation of, for example, Glu side chains at acidic pH, or the deprotonation of, for example, Lys side chains at basic pH. Such effects of low and high pH values on coiled-coil heterodimer formation may be overcome, however, by increasing salt concentration.

Increasing the salt concentration can neutralize the stabilizing ionic attractions or suppress the destabilizing ionic repulsions. Certain salts have greater efficacy at neutralizing the ionic interactions. For example, in the case of the K-coil peptide in FIG. 13A, a 1M or greater concentration of $ClO_4^-$ anions is required to induce maximal α-helical structure, whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer vs. a homodimer.

FIG. 13A shows a biosensor electrode 124 in which the hydrocarbon chain monolayer, indicated at 126 includes a K coil peptide subunits, such as subunit 128, as described above. In the embodiment shown, each peptide subunit is coupled to the electrode surface via a tripeptide spacer, such as spacer 127 in subunit 128, which is itself attached to the electrode surface through a sulfhydryl linkage, as shown. The peptide, including the peptide spacer, is formed conventionally, e.g., by solid phase synthesis. The amount of peptide subunit in the monolayer is about 20 mole percent. The monolayer was formed according to the method described above with respect to FIG. 3C. As indicated above, the peptide subunit may alternatively be coupled to the distal ends of a portion of the hydrocarbon chains in the monolayer, placing the subunit more on the monolayer surface. A hydrocarbon chain-peptide conjugate suitable for this application may be made, for example, by attaching an activated-end hydrocarbon chain to the terminal amino acid of the peptide, as the terminal step in solid phase synthesis.

Presumably because of the positive charge imparted to the monolayer by the K coil subunits, the monolayer shows relatively high conductance to negatively charged redox species, such as $Fe(CN)_6^{3-}$, as evidenced by a relatively high oxidation or reduction current with the redox species.

FIG. 13B shows the same monolayer, but after addition of complementary, negatively charged E coil subunits, such as indicated at 130. As shown, oppositely charged subunits pair to form charge-neutral heterodimers in the monolayer. This pairing is effective to reduce monolayer conductance substantially, as evidenced by the time-dependent fall in measured oxidation or reduction current in the presence of $Fe(CN)_6^{3-}$ ions (FIG. 14).

As shown in FIG. 3C, the second peptide subunit, e.g., the E coil subunit, added to the monolayer may be derivatized with a ligand, producing a monolayer having charge-neutral heterodimers embedded therein (or attached to the monolayer surface), and a ligand exposed on the monolayer surface. The resulting electrode is effective to measure ligand-specific receptor binding events in a biosensor operated in accordance with the invention.

The operating characteristics of such a biosensor are illustrated in FIG. 15. The electrode in this biosensor includes (i) a monolayer with embedded K coils covalently attached to the electrode surface, (ii) complementary E coils forming heterodimers with the K coils in the monolayer, and (iii) surface disaccharide ligands of the type shown in FIG. 6 attached covalently to the E coils and disposed therefore at the monolayer surface. As seen in FIG. 15, addition of the PAK protein receptor (see FIG. 6B) produces a increase in both oxidation and reduction currents, with the current increase over time presumably reflecting additional binding events after receptor addition to the biosensor electrode.

A similar biosensor having a trisaccharide, rather than disaccharide, ligand attached to the E coil subunit in the electrode monolayer was tested with the Verotoxin receptor described above with respect to FIGS. 8A–8C, with the results seen in FIG. 16. The solid lines in the figure show the increase in oxidation and reduction current observed, as a function of time, after addition of Verotoxin.

The following examples are intended to illustrate, but in no way limit the invention.

EXAMPLE 1

Synthesis of Receptors in a Form Suitable for Immobilization on a Gold Electrode Referring to FIGS. 17A–17D and 18, selective tosylation 1,16-dihydroxyhexane provided the monotosylated alcohol 1 in 42% yield. Trisaccharide 2, obtained as described in the literature (Janson, et al., *J. Org. Chem.* 53:5629 (1988)), was converted into an anomeric mixture of trichloroacetamidates 3. Glycosylation of alcohol 1 with glycosyl donor 3 in $CH_2Cl_2$ in the presence of a catalytic amount of trimethylsilyl trifluoromethanesulfonate (TMSOTf) gave trisaccharide glycoside ω-tosylate 4, which was used in the next step without purification. The tosyloxy group of compound 4 was displaced by thiocyanate to provide the trisaccharide glycoside 5, terminated at the reducing end by spacer-arm containing the masked thiol function. Reduction of thiocyanate by the action of sodium borohydride (Olsen, R. K., and Snyder, H. R., *J. Org. Chem.* 30:184 (1965) followed by saponification of acetate groups gave trisaccharide receptor 6.

The disaccharide imidate 7 was reacted with alcohol 1 in a similar fashion to that described for the trisaccharide 4. Synthesis of the disaccharide glycosyl donor 7 is not described here but follows established methods that are considered a general art. Nucleophilic substitution of the tosyloxy group by thiocyanate was carried out as described for preparation of 5 to give compound 8. Reduction of thiocyanate accompanies by deacetylation afforded synthetic disaccharide receptor 9.

A. 16-(p-Toluensulfonyloxy)hexadecanol (Structure 1)

To a solution of 1.1 g of 1,16-dihydroxyhexadecane in 10 ml of dry pyridine 0.8 g of tosyl chloride was added. After 2 h mixture was concentrated diluted with 20 ml of acetone, 5 g of $SiO_2$ was added and acetone was removed in vacuum. The solid was applied on $SiO_2$ and eluted with pentane-ethyl acetate (2:1) to yield 748 mg (42%) of the compound of Structure 1 (C-101).

B. 2,3,4,6-tetra-O-acetyl-D-galactopyranasyl (α1→4)-6-O-acetyl-2,3-di-O-benzoyl-D-galactopyranosyl(β1→4)-2,3,6-tri-O-benzoyl-D-glucopyranosyl (β1→O)-(16-thiocyano) hexadecanol (Structure 5)

A mixture of 277 mg of imidate, 100 mg of C-101 and 0.5 g of mol. sieves (4A) was stirred for 1 h. Then 8 μl of TMSOTf was added. After 2 h 1 ml of EA was added, solid was removed by filtration. Filtrate was concentrated and dried in vacuum. A solution of the residue and 200 mg of KSCN in 6 ml of DMF was stirred at 80° C. for 2 hours. Mixture was concentrated, dissolved in 30 ml of $CH_2Cl_2$, washed with water and concentrated again. Chromatography of the residue on $SiO_2$ with pentane-ethyl acetate (3:2) gave 225 ml (73%) of the compound of Structure 5 (C-105).

C. D-Galactopyranosyl(α1→4)-D-galactopyranosyl (β1→4)-D-glucopyranosyl(β1-O)-(16-thio)hexadecanol (Structure 6)

To a solution of 60 mg of C-105 in 4 ml of dry MeOH ~40 mg of $NaBH_4$ was added Ar. After stirring for 2 h at 45° C. mixture was concentrated and dissolved under gentle reflux in a solution of 50 mg of NaOH in 10 ml of water. After stirring overnight at 45° C., the mixture was neutralized with cationite ($H^+$-form) and applied on extraction medium SEP-PAK (C-18). The cartridge was washed with 20, 40, 50, 80, and 100% solution of MeOH in water. Fractions of 100% MeOH was concentrated to give 24.4 mg (81%) of the compound of Structure 6 (C-106).

D. (16-thiocyano)hexadecanyl 4O-(2-acetamido-3,4,6-tri-O-acetyl-2-D-galactopyranosyl)-2,3,6-O-acetyl-β-D-galactopyranoside C-108 (Structure 8)

Mixture of 100 mg of imidate 7, 68 mg of C-101 and 100 mg of mol. sieves (4A) in 5 ml of $CH_2Cl_2$ was stirred for 1 h. Then 5 μl of TMSOTf was added. After 2 h 1 ml of thyl acetate was added, solid was removed by filtration. Filtrate was concentrated and dried in vacuum. A solution of the residue and 70 mg of KSCN in 3 ml of DMF was stirred at 80° C. for 2 h. Mixture was concentrated, dissolved in 30 ml of $CH_2Cl_2$, washed with water and concentrated again. Chromatography of the residue on $SiO_2$ with pentane-ethyl acetate (2:1) gave 82 mg (70%) of C-108.

E. (16-thiohydroxy)hexadecanyl 4-O-(2-acetamido-2-deoxy-β-D-galactopyranosyl)-β-D-galactopyranoside (Structure 9)

A solution of 54.2 mg of 8 (C-108) and 40 mg of $NaBH_4$ in 3 ml of dry MeOH was refluxed for 2 h then neutralized with ion-exchange resin DOWEX ($H^+$), concentrated and chromatographed on C-18 in $H_2O$ (50:50):100) to yield 19.7 mg (52%) of the compound of Structure 9 (C-111).

EXAMPLE 2

Isolation of Verotoxin Receptor

Shiga-like (Vero) toxin I abbreviated (SLT-I) was purified from *Escherichia coli* JM101 (pJB128) in a simple, one step procedure using solid phase extraction medium CHROMOSORB-P containing covalently coupled synthetic analogs of the toxin's αGal(1,4)βGal (digalactoside) host cell receptors (SYNSORB-P1). Bacteria were grown in baffled Fernbach flasks at 37° C. in carbenicillin- (50 μg/ml) supplemented tryptic soy broth (TSB) containing SYNSORB-P1 (15 g/L) to bind toxin released from growing cells. Late log phase cultures were treated for 30 minutes at 37° C. with Polymyxin B sulfate (0.1 mg/mL) to release intracellular SLT-I and also allow this to bind to the SYNSORB-P1. Next, the SYNSORB-P1 was collected and washed thoroughly with 250 mM NaCl (pH 3.8) to remove cells and cellular debris. The SLT-I was eluted from the washed SYNSORB-P1 using 50 mM Tris base (pH 10) containing 250 mM NaCl (TN) and concentrated using an Amicon ultrafiltration unit. The concentrated SLT-I was stable for weeks at 4° C. and could be frozen for extended periods of time without appreciable loss of activity. On average, 61% (n=10, SD mean=8, range 48% to 76%) of the SLT activity in the original Polymyxin-treated TSB cultures was recovered in the TN fraction eluted from the SYNSORB-P1. SDS-polyacrylamide gel electrophoretic analysis of the SLT-I preparation revealed two prominent Coomassie blue-stained bands. The molecular weight of these two bands was calculated to be 35,000 and 7,500, respectively. The 7.5 KDz band reacted in western immunoblots with SLT-I but not SLT-II B subunit-specific monoclonal antibody. Amino terminal microsequence analysis of both bands confirmed their identity as the A and B subunits of SLT-I. Average yield of SLT-I was 0.32 mg/L (n=8, SD mean=0.3, range 0.1 to 0.8) of TSB culture and its specific activity in the Vero cytotoxicity assay was 4.4 pg/mL/$CD_{50}$. The results demonstrate the utility of SYNSORB in the facile and rapid purification of carbohydrate binding toxins or lectins.

Although the invention has been described with respect to various specific embodiments and methods, it will be appreciated that various modifications and changes can be made without departing from the invention.

What is claimed is:

1. A biosensor apparatus for detecting binding between an oligosaccharide ligand and ligand-specific binding receptor, comprising an electrode including (i) a detection surface, (ii) formed on said detection surface, a close-packed and ordered monolayer comprising hydrocarbon chains anchored at their proximal ends to the detection surface, said chains being sufficiently close-packed and ordered to form an effective barrier to inhibit contact of a redox species, in an aqueous solution in contact with the monolayer, with said detection surface and thereby reduce measurably electron flow across the monolayer mediated by said redox species, and (iii) said oligosaccharide ligand attached to the distal ends of a portion of said chains, such that binding of said ligand-specific binding receptor to said oligosaccharide ligand perturbs the monolayer sufficiently to allow said redox species to contact said detection surface to donate or accept electrons from said surface and thereby increase measurably electron flow across the monolayer mediated by said redox species, a chamber for holding said aqueous solution of redox species in contact with said monolayer, means for introducing said receptor into said chamber, and circuit means, comprising voltage generating means, for measuring electron flow mediated by said redox species across said monolayer, in response to binding occurring between said receptor and said oligosaccharide ligand.

2. The apparatus of claim 1, wherein the detection surface is a gold detection surface and wherein the hydrocarbon chains are 8–22 carbon atom chains anchored at their proximal ends to the detection surface by a thiol linkage.

3. The apparatus of claim 1, wherein said close-packed and ordered monolayer has a molecular density of about 3 to 5 chains/$nm^2$.

4. The apparatus of claim 3, wherein said oligosaccharide ligand is a disaccharide.

5. The apparatus of claim 3, wherein said oligosaccharide ligand is a trisaccharide.

6. The apparatus of claim 5, wherein said ligand-specific binding receptor is a Verotoxin receptor.

7. A biosensor apparatus for detecting binding between an oligosaccharide ligand and ligand-specific binding receptor, comprising an electrode substrate comprising a detection surface, formed on said detection surface, a close-packed and ordered monolayer comprising hydrocarbon chains anchored at their proximal ends to the detection surface, said chains being sufficiently close-packed and ordered to inhibit contact of a redox species, in an aqueous solution in contact with the monolayer, with said detection surface and thereby reduce measurably electron flow across the monolayer mediated by said redox species;

also anchored to the detection surface, a heterodimer-subunit complex composed of first and second peptides that together form α-helical coiled-coil heterodimer, and said oligosaccharide ligand, where (i) said first peptide is covalently bound to the detection surface, (ii) the oligosaccharide ligand is covalently attached to said second peptide;

(iii) binding of said second peptide to said first peptide, to form said heterodimer-subunit complex, is effective to inhibit contact of said redox species with said detection surface and thereby reduce measurably electron flow across the monolayer mediated by said redox species, relative to electron flow observed in the presence of said first peptide alone, and (iv) binding of said ligand-binding receptor to said ligand is effective to allow said redox species to contact said detection surface to donate or accept electrons from said surface and thereby increase measurably the electron flow across the monolayer mediated by said redox species, a chamber for holding said aqueous solution of redox species in contact with said monolayer, means for introducing said receptor into said chamber, and circuit means, comprising voltage generating means, for measuring electron flow mediated by said redox species across said monolayer, in response to binding events occurring between said receptor and said oligosaccharide ligand.

8. The apparatus of claim 7, wherein said oligosaccharide ligand is a disaccharide.

9. The apparatus of claim 7, wherein said oligosaccharide ligand is a trisaccharide.

10. The apparatus of claim 9, wherein said ligand-specific binding receptor is a Verotoxin receptor.

* * * * *